United States Patent
Lee et al.

(10) Patent No.: US 11,065,043 B2
(45) Date of Patent: Jul. 20, 2021

(54) ANTERIOR CERVICAL SPINE PLATE

(71) Applicant: L&K BIOMED CO., LTD., Gyeonggi-do (KR)

(72) Inventors: Jae Shik Lee, Gyeonggi-do (KR); Sang Soo Lee, Gyeonggi-do (KR)

(73) Assignee: L&K BIOMED CO., LTD., Yongin-si (KR)

( * ) Notice: Subject to any disclaimer, the term of this patent is extended or adjusted under 35 U.S.C. 154(b) by 190 days.

(21) Appl. No.: 16/346,845

(22) PCT Filed: Nov. 3, 2017

(86) PCT No.: PCT/KR2017/012423
§ 371 (c)(1),
(2) Date: May 1, 2019

(87) PCT Pub. No.: WO2018/084641
PCT Pub. Date: May 11, 2018

(65) Prior Publication Data
US 2019/0314068 A1    Oct. 17, 2019

(30) Foreign Application Priority Data
Nov. 3, 2016   (KR) .......................... 10-2016-0145815

(51) Int. Cl.
*A61B 17/80* (2006.01)
*A61B 17/70* (2006.01)

(52) U.S. Cl.
CPC ...... *A61B 17/8042* (2013.01); *A61B 17/7059* (2013.01)

(58) Field of Classification Search
CPC ........................ A61B 17/7059; A61B 17/8042
See application file for complete search history.

(56) References Cited

U.S. PATENT DOCUMENTS 6,413,259 B1 * 7/2002 Lyons ................ A61B 17/8042
606/295
7,666,185 B2    2/2010 Ryan et al.
(Continued)

FOREIGN PATENT DOCUMENTS

| KR | 10-1074180 B1 | 10/2011 |
| KR | 10-2012-0082396 A | 7/2012 |
| WO | 99/56653 A1 | 11/1999 |

OTHER PUBLICATIONS

English translation of International Search Report issued in PCT/KR2017/012423, dated Feb. 14, 2018.

*Primary Examiner* — Nicholas W Woodall
(74) *Attorney, Agent, or Firm* — Medler Ferro Woodhouse Mills PLLC

(57) ABSTRACT

The present invention relates to an anterior cervical spine plate which is used to perform anterior fixation surgery on a cervical spine in orthopedic surgery and neurosurgery, which includes: a plate body formed to extend in a longitudinal direction thereof; two or more bone screw holes formed in the plate body to support head parts of bone screws; and a locking element configured to maintain the bone screws while being inserted into the bone screw holes, respectively. The locking element is rotatably coupled to the plate body, and the plate body has reinforcing parts formed at outer circumferences thereof.

21 Claims, 9 Drawing Sheets

(56) References Cited

U.S. PATENT DOCUMENTS

| | | | |
|---|---|---|---|
| 8,652,182 B1* | 2/2014 | Walker | A61B 17/8052 606/296 |
| 2003/0040749 A1* | 2/2003 | Grabowski | A61B 17/7059 606/71 |
| 2005/0075633 A1* | 4/2005 | Ross | A61B 17/8033 606/280 |
| 2008/0021470 A1 | 1/2008 | Ross | |
| 2008/0091206 A1* | 4/2008 | Johnson | A61B 17/8042 606/246 |
| 2011/0022097 A1* | 1/2011 | Walker | A61B 17/8033 606/296 |
| 2014/0276829 A1* | 9/2014 | Hershgold | A61B 17/8023 606/71 |

* cited by examiner

ANTERIOR CERVICAL SPINE PLATE

TECHNICAL FIELD

The present invention relates to an anterior cervical spine plate, and more particularly to an anterior cervical spine plate which is used to perform anterior fixation surgery on a cervical spine in orthopedic surgery and neurosurgery.

BACKGROUND ART

In general, patients having spinal disorders such as cervical disc disease, cervical herniated disc, cervical fracture and dislocation, and cervical spondylosis myelopathy, are subjected to treatment and correction by fixing the respective cervical spines so as not to be moved relative to each other. For this, a cervical fixation device has been widely used for fixing the cervical spines during fusion in the art.

A cervical plate generally refers to an implantation plate used for treatment of spinal disorders. The cervical plate is inserted in a manner of anteriorly approaching cervical spines, and serves to support two or more cervical spines when fusing upper and lower cervical spines. In general, the cervical plate is fixed to the anterior cervical spine by inserting bone screws into bone screw holes formed in the cervical plate, and fastening the bone screws so that heads thereof press the cervical plate against the cervical spines. In addition, the cervical plate is curved at an angle similar to a lordosis of the cervical spines, thereby having a shape that is in close contact with the anterior cervical spine during surgery.

Further, if the bone screw is separated from the cervical plate, it may be fatal to the patient, such that a locking element is installed in a cervical fixation device to prevent the bone screw from being separated from the cervical plate. As a conventional technique for preventing such a separation, there are various methods such as a method (see U.S. Pat. No. 5,364,399) in which a separation prevention screw for covering a portion of the head of the bone screw is additionally attached to the cervical plate so as to prevent the bone screw from being separated from the cervical plate, a method (see U.S. Pat. No. 6,193,721) of using a rotatable locking element which is integrally fixed to the cervical plate and the like.

However, in the conventional techniques, a method for resolving foreign body sensation felt by the patient after the surgery has not been considered.

PRIOR ART DOCUMENT

Patent Document (Patent Document 1) U.S. Pat. No. 5,364,399
(Patent Document 2) U.S. Pat. No. 6,193,721

SUMMARY OF INVENTION

Problems to be Solved by Invention

It is an object of the present invention to provide an anterior cervical spine plate that may be easily used by a doctor during surgery, and may improve surgery prognosis of a patient by solving a foreign body sensation felt by the patient after the surgery.

Means for Solving Problems

To achieve the above objects, according to the present invention, there is provided a cervical plate including: a plate body formed to extend in a longitudinal direction thereof two or more bone screw holes formed in the plate body to support head parts of bone screws; and a locking element configured to maintain the bone screws while being inserted into the bone screw holes, respectively, wherein the locking element is rotatably mounted in the plate body.

The plate body may have reinforcing parts formed at outer circumferences thereof.

In addition, the plate body may have round parts formed at opposite ends in a longitudinal direction thereof.

Further, the round part may be formed of two curved surfaces having different radii of curvature.

When a radius of curvature of a curved surface located at an upper end of the plate body is R1, a radius of curvature of a curved surface located at a lower end of the plate body is R2, a radius of a shank of the bone screw to be inserted into the bone screw hole is L1, and the shortest distance from a central axis of the bone screw to the end of the plate body is L2, the R1, R2, L1 and L2 may satisfy Equation 1 below, and R2 may be smaller than R1:

$$0.5 \leq \frac{R2 \times L1}{R1 \times L2} \leq 250 \qquad \text{[Equation 1]}$$

Further, the plate body may have seat parts formed at regions, in which the bone screw holes and the locking elements are disposed, having a thickness thinner than other parts thereof.

Further, the seat part may have a depth of less than or equal to a maximum thickness of the locking element.

Further, the plate body may have a bending clearance part formed on a lower surface thereof in a direction perpendicular to the longitudinal direction of the plate body.

Further, the bending clearance part may have a depth of 0.1 to 0.3 times the thickness of the plate body.

Further, when a curvature of the plate body between the locking elements located at opposite ends in the longitudinal direction thereof is R3, and curvatures of the plate body from the locking elements located at opposite ends to the ends thereof are R4 and R5, respectively, the R4 and R5 may be smaller than the R3.

Further, the R4 and R5 may be different from each other.

Further, the R4 and R5 may be within ranges of $5 \leq R3/R4 \leq 44$, and $5 \leq R3/R5 \leq 44$.

Further, when lengths of the plate body occupied by R3, R4 and R5 in the longitudinal direction thereof are L3, L4 and L5, respectively, the L3, L4 and L5 may have a ratio of L3:L4:L5=3-5:1:0.8-1.2.

Further, the locking element may include a rotation body rotatably mounted in the plate body; and a locking wing formed integrally with the rotation body to cover a portion of the bone screw hole.

Further, the rotation body may have a tool guide hole formed inside thereof, and a locking tool groove formed on an upper periphery of the tool guide hole concentrically with the tool guide hole.

Further, the locking wing may have a rotation contact circumference formed on one side thereof concentrically with the rotation body, and a locking contact circumference formed thereon continued to the rotation contact circumference, such that two adjacent locking elements may be independently rotatable in the bone screw hole with abutting each other by the rotation contact circumferences, and further rotation thereof may be blocked when the locking contact circumferences are in contact with each other.

Further, the locking wing may have a rotation stop circumference formed thereon continued to the locking contact circumference, and a distance between a central axis of the rotation body and the rotation stop circumference may be larger than a radius of curvature of the rotation contact circumference.

Further, the locking wing may be resiliently deformed with being in contact with a seat part, and may be restored to an original shape by an elastic force when covering a portion of the bone screw hole.

Further, the plate body may include the seat parts formed at regions, in which the bone screw holes and the locking elements are disposed, having a thickness thinner than other parts thereof, wherein a locking element beginning part may be formed on a lower surface of the locking wing, and a body plate beginning part may be formed on one side of the seat part, and wherein an open state of the locking element may be maintained by an engagement between the body plate beginning part and the locking element beginning part unless an external force is applied thereto.

Further, the plate body may have an end stopper formed thereon to restrict a rotation of the locking element.

Further, a body plate finishing part may be formed on the end stopper, a locking element finishing part may be formed on a lower surface of the locking wing, and a locked state of the locking element may be maintained by the engagement of the body plate finishing part and the locking element finishing part unless an external force is applied thereto.

Furthermore, the plate body may have a locking jaw formed thereon in a chevron shape, so as to allow the locking wing of the locking element to climb over the locking jaw while being in contact therewith.

Advantageous Effects

The present invention prevents the patient from feeling the foreign body sensation after the surgery. In addition, the locking element that supports the bone screw so as not to be separated allows the cervical plate to maintain a position thereof, such that it is possible to prevent the bone screw from being separated from the cervical spine plate after the surgery.

As a result, a product completeness of the cervical plate may be improved, and a reliability from a patient and an operator may be enhanced.

MODE FOR CARRYING OUT INVENTION

Figure 1:
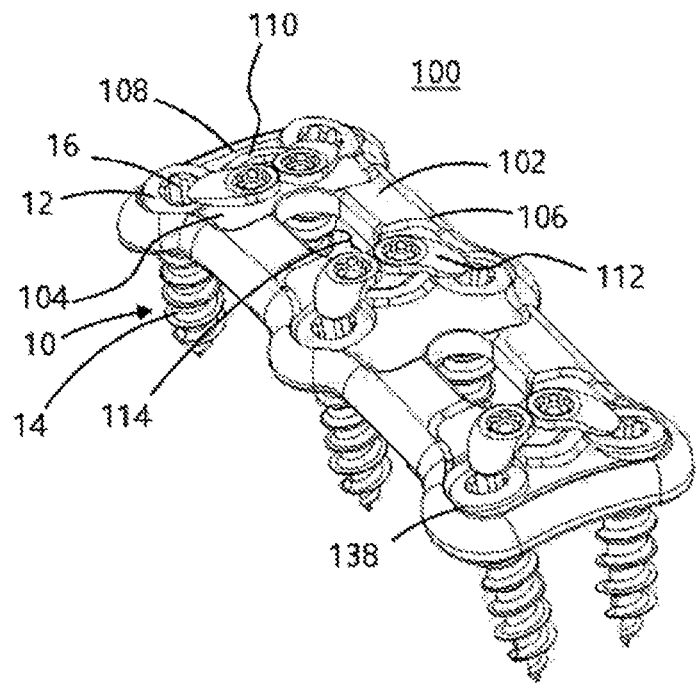
FIG. 1 is a perspective view illustrating a cervical plate according to Embodiment 1 of the present invention.

Hereinafter, the present invention will be described in detail with reference to the accompanying drawings. In denoting reference numerals to constitutional elements of respective drawings, it should be noted that the same elements will be denoted by the same reference numerals although they are illustrated in different drawings. In the embodiments of the present invention, the publicly known functions and configurations that are judged to be able to make the purport of the present invention unnecessarily obscure will not be described.

Figure 2:
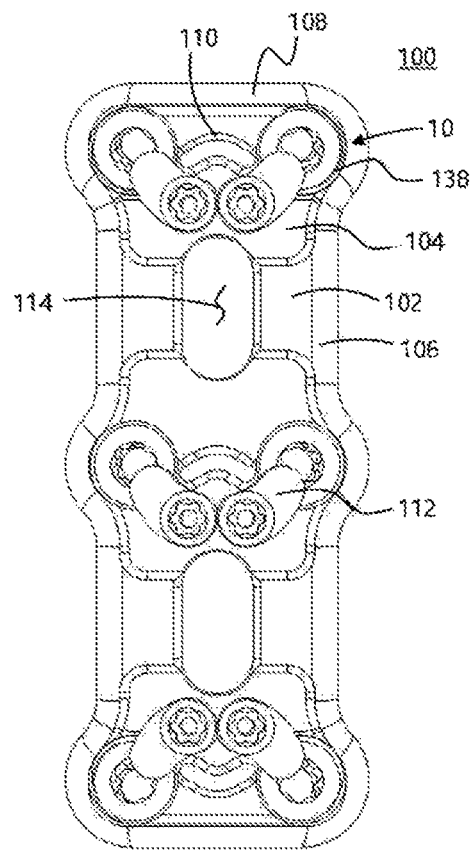
FIG. 2 is a plan view illustrating the cervical plate of FIG. 1.

A cervical plate 100 according to Embodiment 1 of the present invention will be described with reference to FIGS. 1 to 15. As illustrated in FIGS. 1 and 2, the cervical plate 100 basically includes a plate body 102 formed to extend in a longitudinal direction, two or more bone screw holes 138 formed in the plate body 102 to support head parts 12 of bone screws 10, and a locking element 112 configured to maintain the bone screws 10 having threads 14 formed thereon while being inserted into the bone screw holes 138, respectively.

The cervical plate 100 may be made of a known material such as titanium, or a Co—Cr alloy, but it is not limited thereto.

The locking element 112 is rotatably coupled to the plate body 102, and the plate body 102 may have reinforcing parts 106 formed at outer circumferences thereof.

The reinforcing part 106 is thicker than or equal to that of the plate body 102, and has a curved surface toward an outside, thereby serving to enhance the rigidity against a stress acting thereon in various directions such as bending and twisting forces.

In addition, round parts 108 may be formed at opposite ends in a longitudinal direction of the plate body 102. The round part 108 has a shape in which, when the cervical plate 100 is installed on the cervical spines, a slope from a surface of the cervical spine to an upper surface of the plate body 102 is gentle, so as to reduce a foreign body sensation that may be felt by a patient after the surgery.

Figure 12:
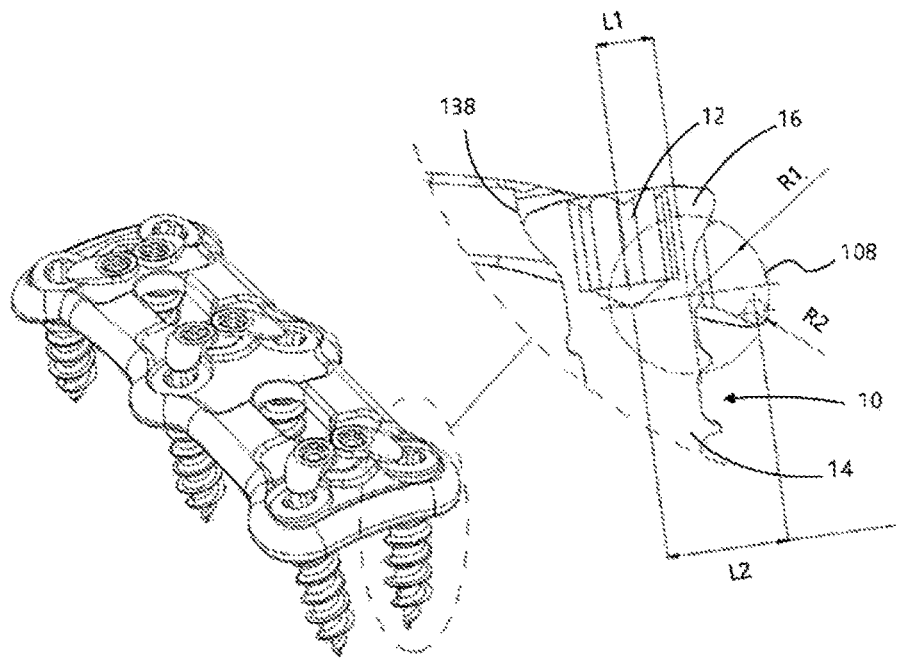
FIG. 12 is a partial enlarged cross-sectional view illustrating a state in which bone screws are inserted in the cervical plate of FIG. 1.

To this end, it is preferable that the round part 108 is formed of two curved surfaces having different radii of curvature. As illustrated in FIG. 12, when a radius of curvature of a curved surface located at an upper end of the plate body 102 is R1, a radius of curvature of a curved surface located at a lower end of the plate body 102 is R2, a radius of a shank of the bone screw 10 to be inserted into the bone screw hole 138 is L1, and the shortest distance from a central axis of the bone screw 10 to the end of the plate body 102 is L2, it is preferable that the R1, R2, L1 and L2 satisfy Equation 1 below. At this time, R1 is larger than R2.

$$0.5 \leq \frac{R2 \times L1}{R1 \times L2} \leq 250 \quad \text{[Equation 1]}$$

The reinforcing part 106 and the round part 108 may be formed together as in Embodiment 1, but these parts may be optionally formed.

In addition, the plate body 102 may have seat parts 104 formed at regions, in which the bone screw holes 138 and the locking elements 112 are disposed, having a thickness thinner than other parts thereof. The seat part 104 serves to suppress the foreign body sensation that may be felt by the patient due to the thickness of the locking element 112 which is attached to the plate body 102. Thus, considering the overall thickness of the cervical plate, it is ideal that the maximum depth of the seat part 104 is less than or equal to the maximum thickness of the locking element 112. Herein, the locking element 112 may protrude slightly compared to the surface of the plate body 102 depending on a design.

Figure 3:
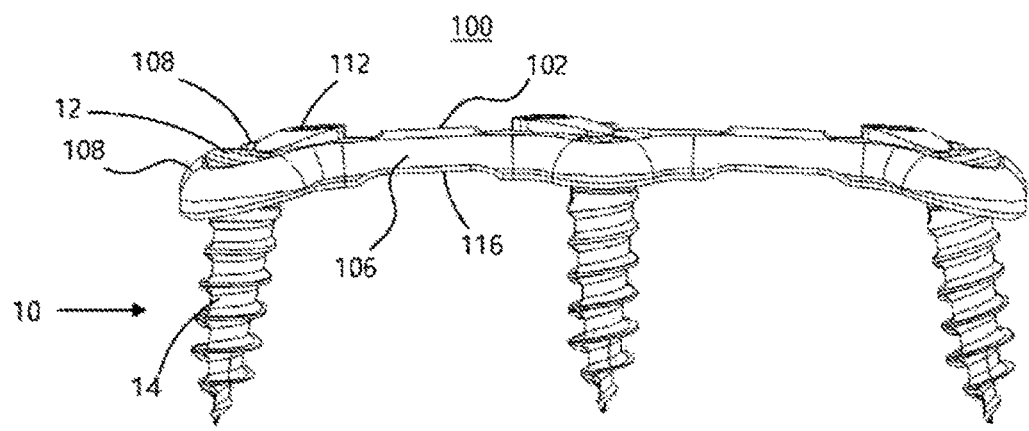
FIG. 3 is side view illustrating the cervical plate of FIG. 1.
Figure 4:
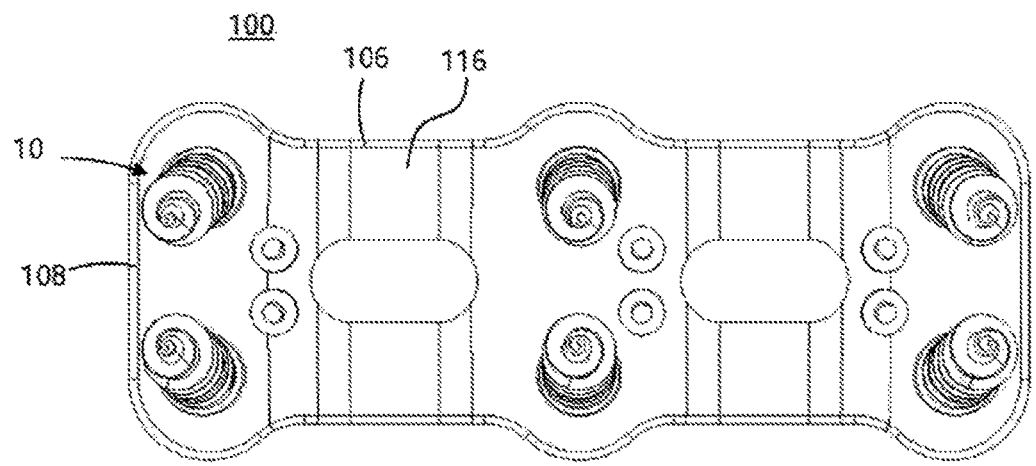
FIG. 4 is a bottom view illustrating the cervical plate of FIG. 1.

In addition, the plate body 102 may have a bending clearance part 116 formed on a lower surface thereof in a direction perpendicular to the longitudinal direction of the plate body 102. Generally, spinal shapes are different for each patient, such that the cervical plate 100 is often used by bending so as to coincide with the spinal shape of the patient during surgery. At this time, since the cervical plate 100 is made of a material such as titanium, bending is not easy and a large force is required for bending. Therefore, in Embodiment 1, as illustrated in FIGS. 3 and 4, by forming the bending clearance part 116 on the lower surface of the plate body 102, bending of the cervical plate 100 may be facilitated.

However, when arranging three pairs of bone screw holes 138, the bending clearance parts 116 are formed between adjacent two pairs of bone screw holes 138. In particular, it is preferable that the bending clearance parts are disposed to avoid the seat parts 104.

The bending clearance part 116 may have a depth of 0.1 to 0.3 times the thickness of the plate body, so that bending of the cervical plate may be facilitated without largely affecting a strength thereof.

In addition, the plate body 102 may have cutoff parts 114 formed therein, which are capable of reducing a weight thereof, dispersing the stress, and serving as a window for confirming a vertebra surface contacting therewith during surgery. The cutoff part 114 may be formed at a position where the bending clearance part 116 is formed.

Figure 13:
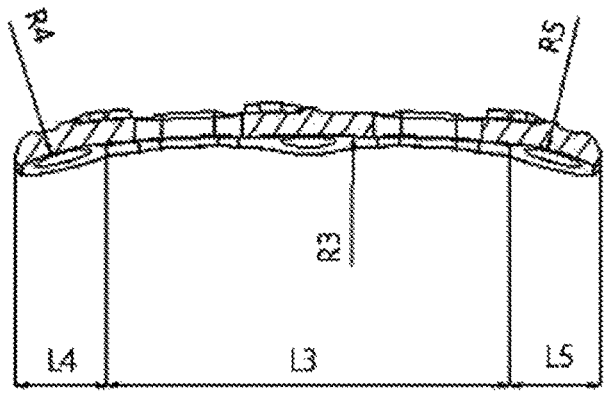
FIG. 13 is a side view illustrating a side curvature of the cervical plate of FIG. 1.
Figure 14:
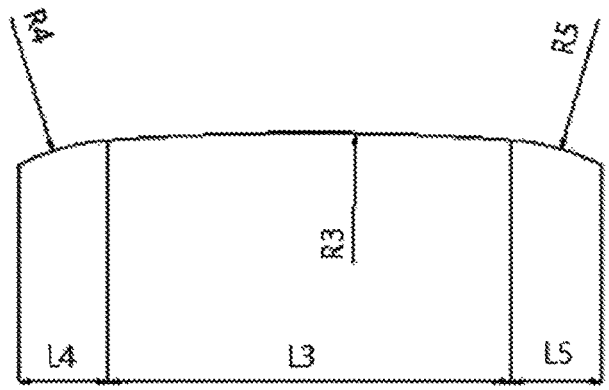
FIG. 14 is a schematic view illustrating only the curvature in FIG. 13.

In addition, in order for the plate body 102 to come into close contact with vertebrae, as illustrated in FIGS. 13 and 14, when a curvature of the plate body 102 between the locking elements 112 located at opposite ends in the longitudinal direction thereof is R3, and curvatures of the plate body from the locking elements 112 located at opposite ends to the ends thereof are R4 and R5, respectively, by setting R4 and R5 to be smaller than R3, it is possible to correspond to an entire curved shape of the R3 region of a central portion and vertebrae located at upper and lower portions thereof.

Further, it is possible to form R4 and R5 to be different from each other depending on the curvature of the vertebra. In this case, the R4 and R5 may be determined within ranges of $5 \leq R3/R4 \leq 44$, and $5 < R3/R5 < 44$.

In addition, when lengths of the plate body 102 occupied by R3, R4 and R5 in the longitudinal direction thereof are L3, L4 and L5, respectively, if setting L4 to be 1, it is possible to design the L3, L4 and L5 to have a ratio in a range of L3:L4:L5=3-5:1:0.8-1.2.

Figure 5:
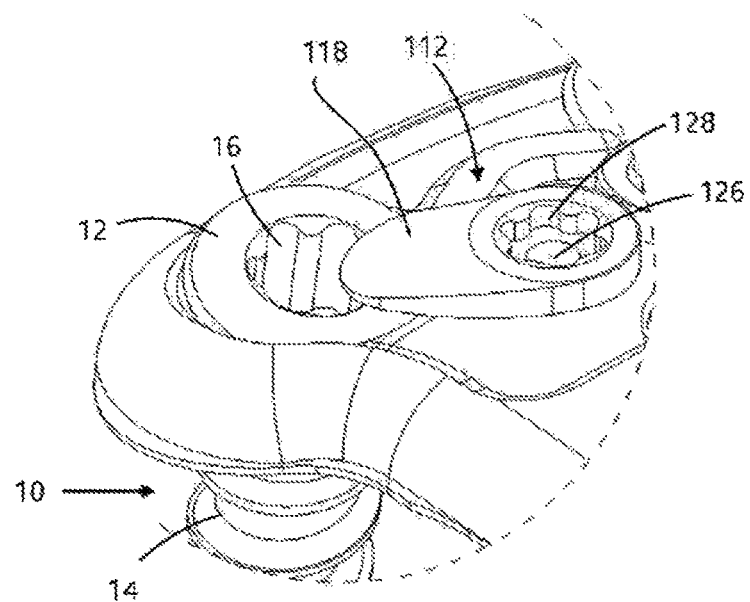
FIG. 5 is a partial enlarged perspective view illustrating the cervical plate of FIG. 1.
Figure 6:
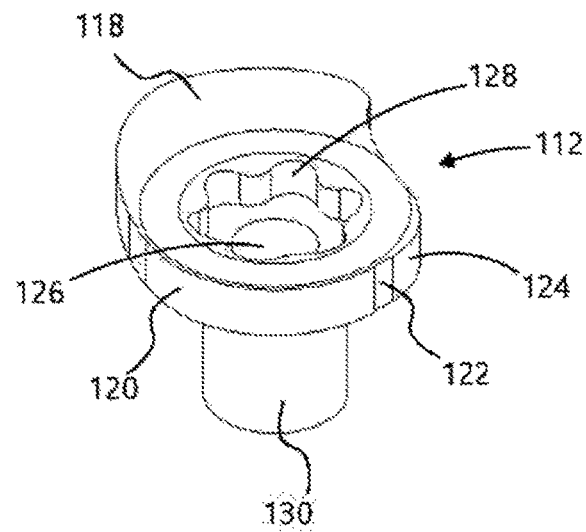
FIG. 6 is a perspective view illustrating a locking element of the cervical plate of FIG. 1.

As illustrated in FIGS. 5 and 6, the locking element 112 may include a rotation body 130 rotatably mounted in the plate body 102, and a locking wing 118 formed integrally with the rotation body 130 to cover a portion of the bone screw hole 138.

Figure 9:
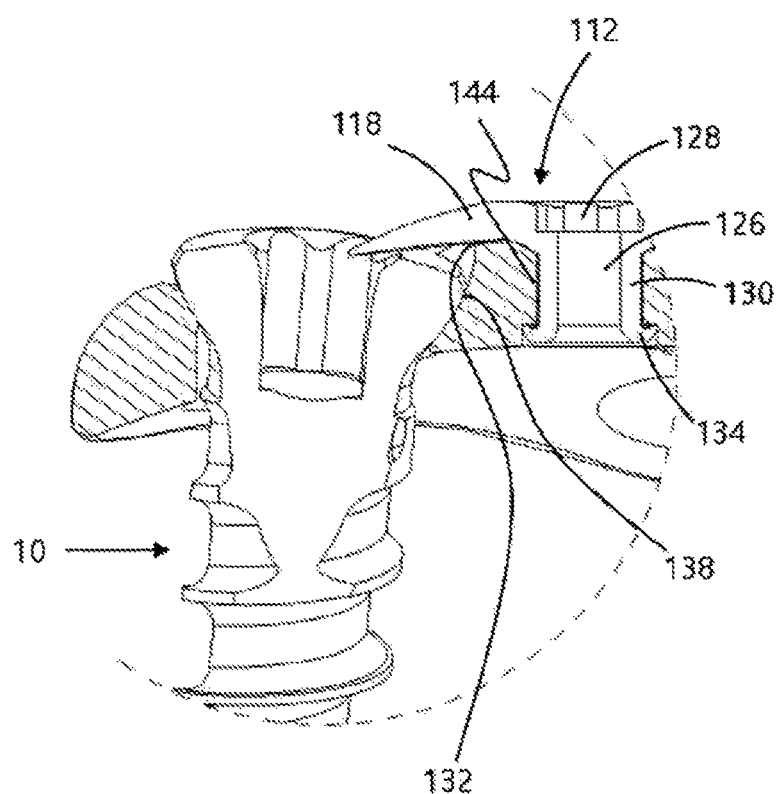
FIG. 9 is a partial enlarged cross-sectional view illustrating a locked state in the cervical plate of FIG. 1.
Figure 15:
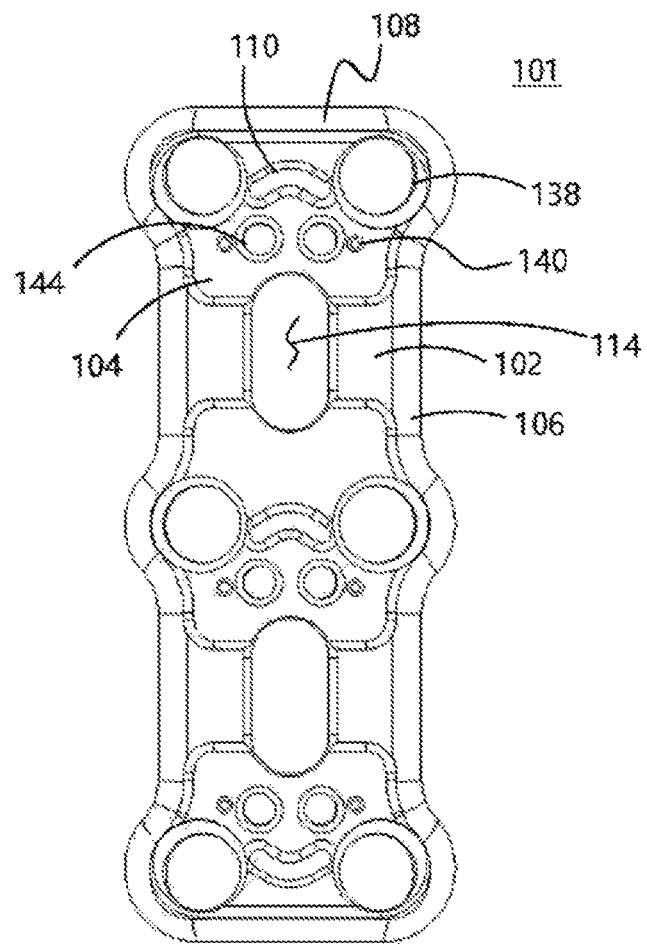
FIG. 15 is a plan view illustrating a cervical plate according to Embodiment 2 of the present invention.

As illustrated in FIG. 15, the rotation body 130 is inserted and placed into a locking element insertion hole 144, such that the locking element 112 is rotatably installed therein. FIG. 15 is a view of Embodiment 2, but the locking element insertion hole 144 is the same as Embodiment 1, and therefore will be described with reference to FIG. 1. As illustrated in FIG. 9, the rotation body 130 is passed through the locking element insertion hole 144, and then the rotation body 130 is maintained therein by striking an end portion thereof to be enlarged and formed in a latching part 134.

The locking elements 112 are arranged one by one for each bone screw 10. In addition, two locking elements 112 are arranged so as to come into contact with each other for a pair of bone screw holes 138 arranged in the direction perpendicular to the longitudinal direction of the plate body 102. That is, the locking wing 118 has a rotation contact circumference 120 formed on one side thereof concentrically with the rotation body 130, and a locking contact circumference 122 formed thereon continued to the rotation contact circumference 120. As a result, two adjacent locking elements 112 are independently rotatable with abutting each other by the rotation contact circumferences 120, and further rotation thereof is blocked in a state in which the locking contact circumferences 122 are in contact with each other. Therefore, in order to prevent the locking elements 112 from rotating while the locking contact circumferences 122 are in contact with each other, a distance between a central axis of the rotation body 130 and the locking contact circumference 122 is formed to be larger than a radius of curvature of the rotation contact circumference 120, such that the locking contact circumferences 122 press against each other with a force applied thereto, and thereby increasing a frictional force therebetween to maintain the locked state.

For prevention of such a rotation, the locking wing 118 has a rotation stop circumference 124 formed thereon continued to the locking contact circumference 122. In this case, a distance between the central axis of the rotation body 130 and the rotation stop circumference 124 is formed to be larger than the radius of curvature of the rotation contact circumference 120 as well as the distance between the central axis of the rotation body 130 and the locking contact circumference 122.

In other words, it is also possible to allow the rotation of the locking element 112 only within a certain range, and to maintain the locked state by forming the outer circumferences of the locking element 112 different in a curved shape like a cam.

Since the locking element 112 is thin, there is a possibility that a tool slips when rotating it by a tool or the like. For prevention of the slip, in the locking element 112, the rotation body 130 has a tool guide hole 126 formed inside thereof, and a locking tool groove 128 formed on an upper periphery of the tool guide hole 126 concentrically with the tool guide hole 126.

Figure 7:
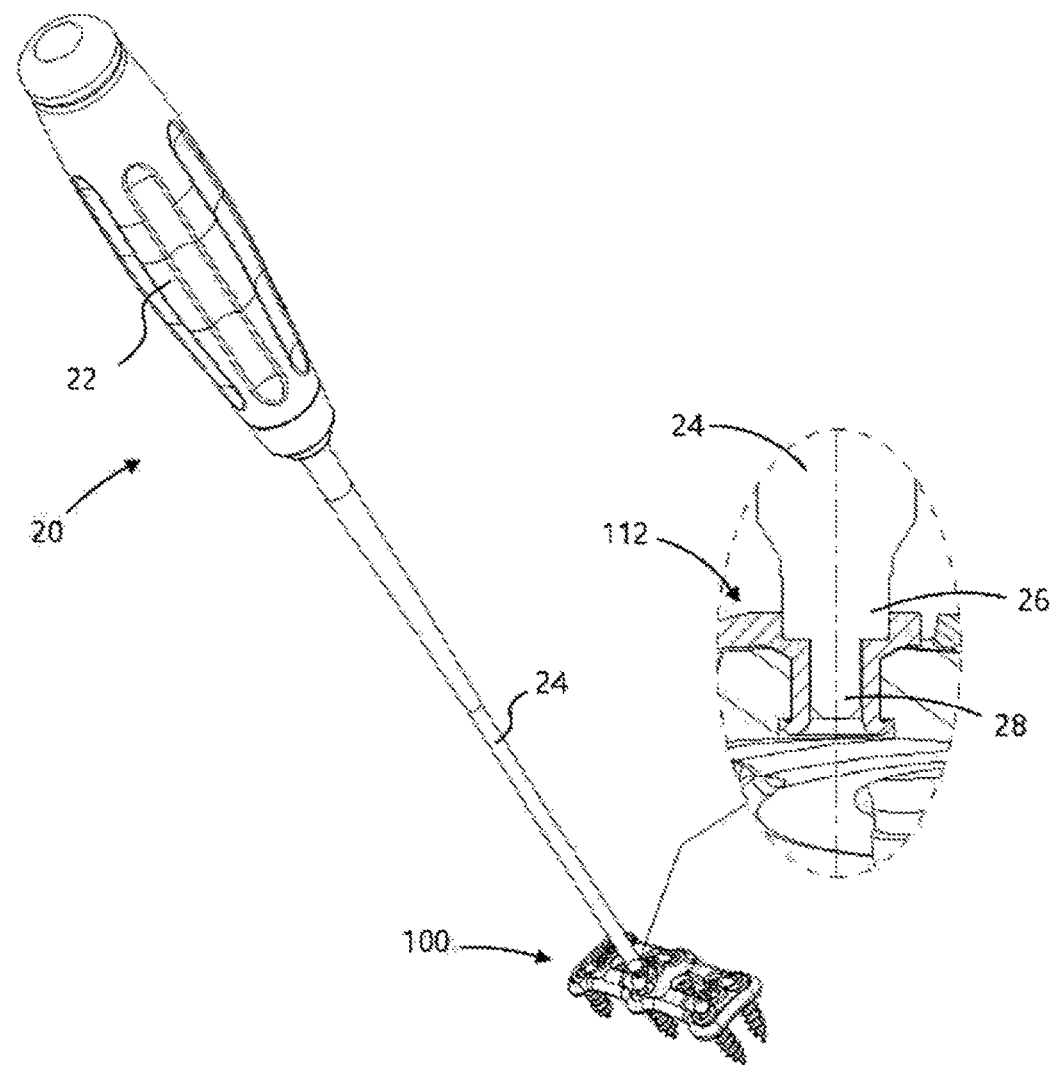
FIG. 7 is a perspective view illustrating a state of operating the locking element of the cervical plate using a tool of FIG. 1.
Figure 8:
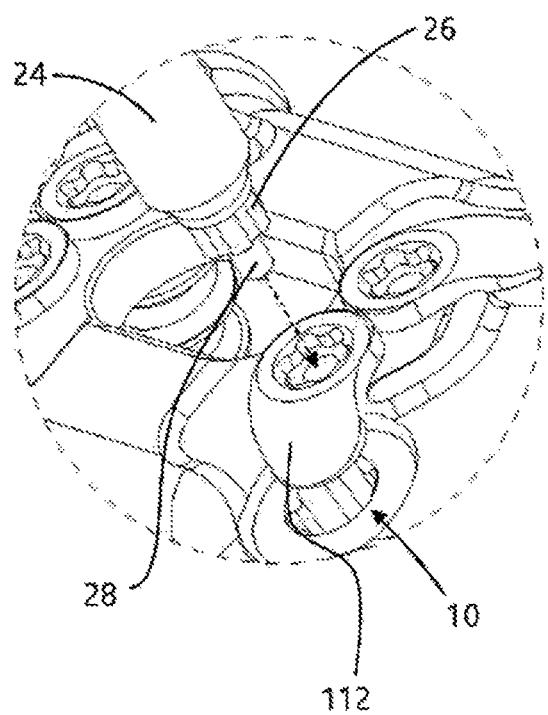
FIG. 8 is a perspective view illustrating a state of attaching and detaching the tool to and from the locking element of the cervical plate of FIG. 1.

Further, in order to correspond to the locking element, as illustrated in FIGS. 7 and 8, a tool 20 is fabricated so as to include a tool rod 24, a tool handle 22 connected to one end of the tool rod 24, a tool tip 26 formed at the other end of the tool rod 24 to be engaged to the locking tool groove 128 and rotate the same, and a tool tip guide 28 which extends from the tool tip 26 to be inserted into the tool guide hole 126.

Therefore, to insert the tool 20, when inserting the tool tip guide 28 into the tool guide hole 126 and slightly turning the tool handle 22 so that the tool tip 26 is engaged to the locking tool groove 128, and then rotating the tool handle 22, the locking element 112 may be stably rotated to be switched between an open state and a locked state.

Figure 10:
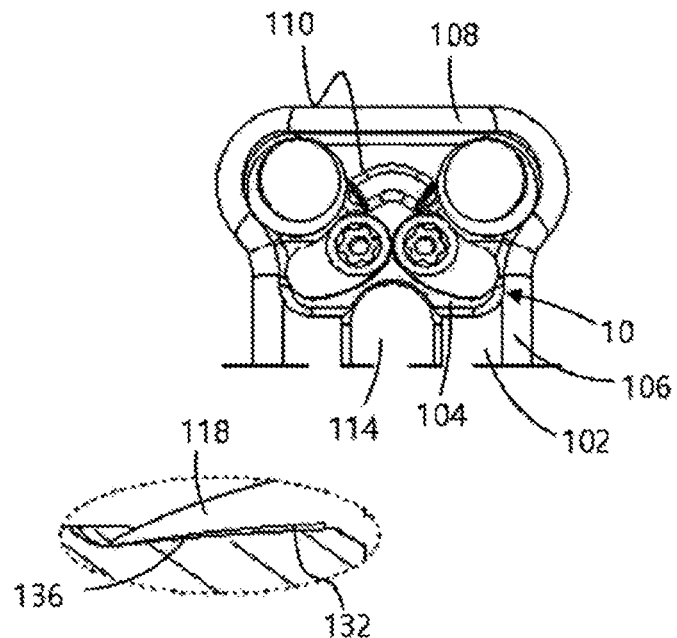
FIG. 10 is a partial enlarged plan view and a cross-sectional view illustrating an open state in the cervical plate of FIG. 1.
Figure 11:
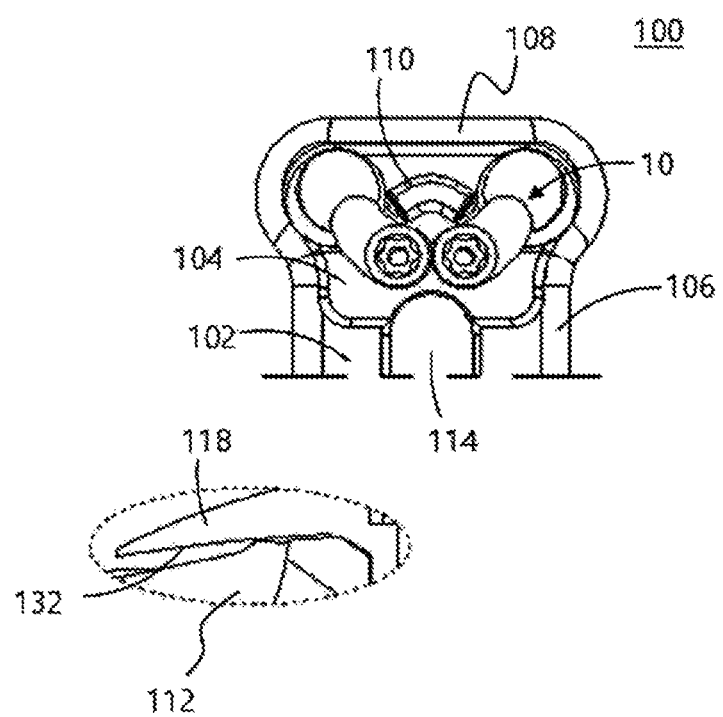
FIG. 11 is a partial enlarged plan view and a cross-sectional view illustrating the locked state in the cervical plate of FIG. 1.

In order to ensure the locking element 112 to maintain the locked state, as illustrated in FIGS. 10 and 11, the locking wing 118 is resiliently deformed when a wing bottom 132 is in contact with a concave surface 136 of the seat part 104, and is restored to an original shape by an elastic force when covering a portion of the bone screw hole 138. Therefore, in the locked state, as illustrated in FIG. 9, an end of the locking wing 118 comes into contact with a head part 12 of the bone screw 10 while being inserted into a head tool groove 16 formed in the head part 12, thereby it is possible to prevent the bone screw 10 from being released.

In addition, end stoppers 110 may be further disposed on the seat parts 104. The end stopper 110 is a structure such as a protrusion that may limit the rotation of the locking element 112, and is disposed in consideration of a rotation locus of the locking element 112. In Embodiment 1, the end stopper 110 is disposed at a position offset to an outside in the longitudinal direction (end direction) of the plate body 102 between a pair of adjacent bone screw holes 138.

As a result, even if applying an additional force to the locking element 112, the rotation of the locking element 112 is limited by the end stopper 110.

Figure 16:
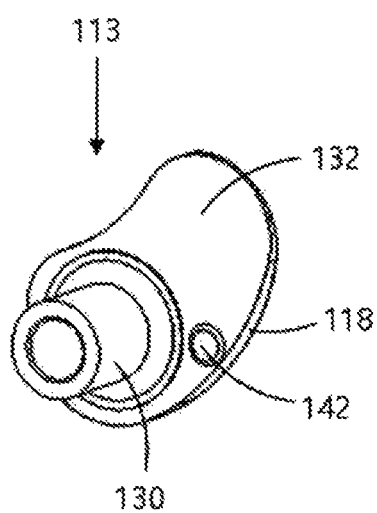
FIG. 16 is a perspective view illustrating a locking element of the cervical plate of FIG. 15.

Next, a cervical plate 101 according to Embodiment 2 of the present invention will be described with reference to FIGS. 15 and 16. The cervical plate 101 is basically the same as the cervical plate 100 according to Embodiment 1, but is characterized in that it may maintain an initial position (open state) of the locking element 113. The same reference numerals are used for the same parts as those in Embodiment 1, and will not be described.

In the locking element 113, a locking element beginning part 142 is formed on the wing bottom 132 of the locking wing 118, and a body plate beginning part 140 corresponding to the locking element beginning part 142 is formed on the seat part 104.

One part of the body plate beginning part 140 and the locking element beginning part 142 is provided with a protrusion and the other part is provided with a concave groove. As a result, the initial position (the open state) of the locking element 113 may be maintained by the coupling force between the body plate beginning part 140 and the locking element beginning part 142 unless an external force is applied thereto.

Figure 17:
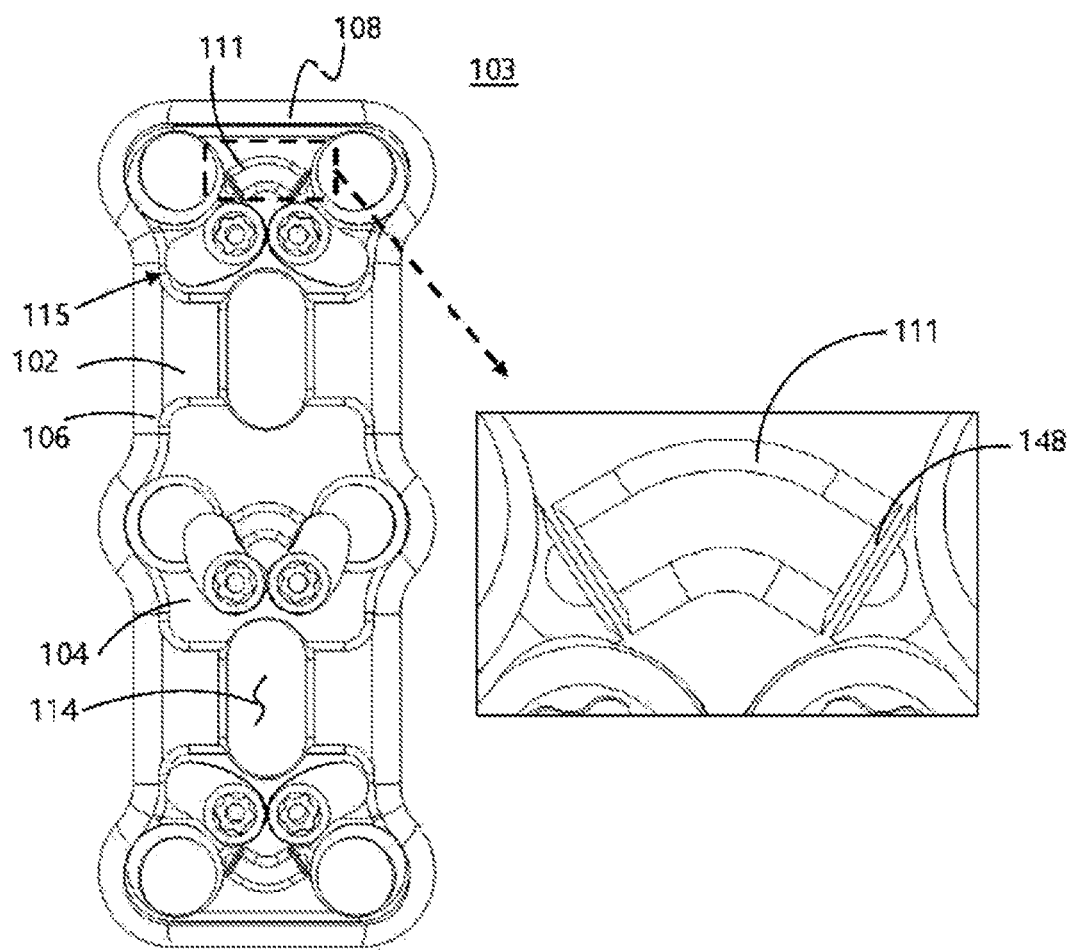
FIG. 17 is a plan view and a partial enlarged plan view illustrating a cervical plate according to Embodiment 3 of the present invention.
Figure 18:
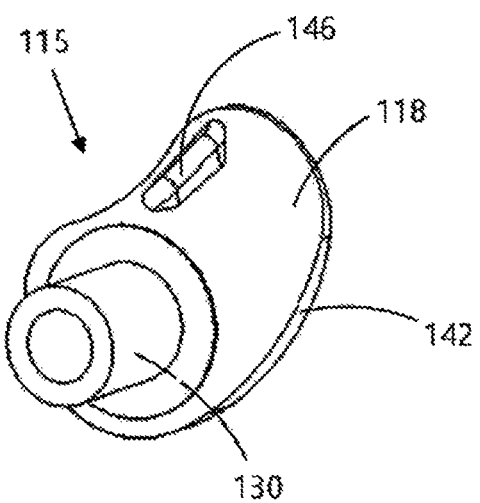
FIG. 18 is a perspective view illustrating a locking element of the cervical plate of FIG. 17.

Next, a cervical plate 103 according to Embodiment 3 of the present invention will be described with reference to FIGS. 17 and 18. The cervical plate 103 is basically the same as the cervical plate 100 according to Embodiment 2, but is characterized in that a final position (the locked state) of the locking element 115 may be maintained. The same reference numerals are used for the same parts as those in Embodiment 1, and will not be described.

A body plate finishing part 148 is formed on the end stopper 111, and a locking element finishing part 146 is formed on a lower surface of the locking wing 118 of the locking element 115. When rotating the locking element 115 by the tool 20, the locking element finishing part 146 is engaged to the body plate finishing part 148 passing through an inclined surface of the end stopper 111. Therefore, the locked state of the locking element 115 may be maintained by the engagement of the body plate finishing part 148 and the locking element finishing part 146 unless an external force is applied thereto.

Figure 19:
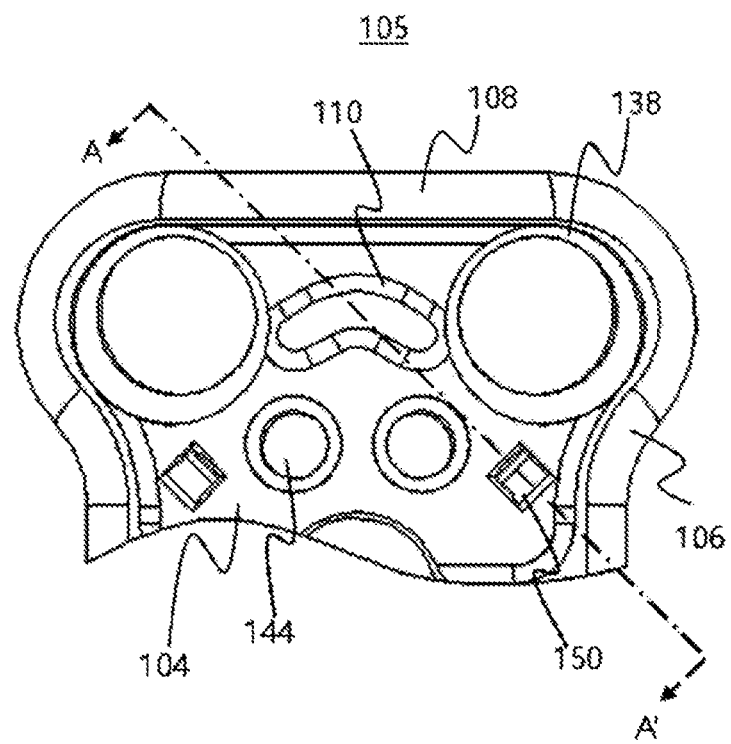
FIG. 19 is a partial plan view illustrating a cervical plate according to Embodiment 4 of the present invention.
Figure 20:
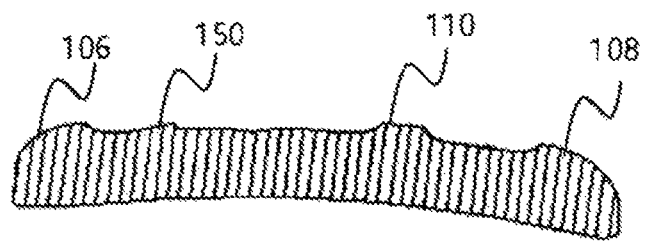
FIG. 20 is a cross-sectional view taken on line A-A' in FIG. 19.

Further, a cervical plate 105 according to Embodiment 4 of the present invention will be described with reference to FIGS. 19 and 20. The cervical plate 105 is basically the same as the cervical plate 100 according to Embodiment 1, but is characterized in that the initial position (open state) and the final position (locked state) of the locking element 113 may be maintained. The same reference numerals are used for the same parts as those in Embodiment 1, and will not be described.

To this end, the same locking element 112 as Embodiment 1 is used, and a locking jaw 150 is further formed on the seat part 104 of the plate body 102. The locking jaw 150 may be formed in a chevron shape of a sawtooth form whose one side is a gentle slope and the other side is a steep slope, so as to allow the locking wing 118 to climb over the locking jaw when rotating the locking element, but prevent the locking wing 118 from being rotated to a direction opposite to the rotation when the locking wing 118 completely passes over the locking jaw 150.

Accordingly, when the locking element 112 is opened by the locking jaw 150, in order to climb over the locking jaw 150, it is necessary to apply a force so as to be slightly deformed, such that the locking jaw 150 may maintain the open state unless applying the force. Further, when the locking element 112 completely passes over the locking jaw 150, the locking element 113 is caught by the locking jaw 150 so as to block the locking element from being rotated to the direction opposite to the rotation. As a result, the locked state may be maintained.

It is also possible that all the characteristics of the above-described Embodiments 1 to 4 are included in one cervical plate or optionally included therein.

While the present invention has been described with reference to the preferred embodiments and modified examples, the present invention is not limited to the above-described specific embodiments and the modified examples, and it will be understood by those skilled in the related art that various modifications and variations may be made therein without departing from the scope of the present invention as defined by the appended claims.

DESCRIPTION OF REFERENCE NUMERALS

1: Vertebra
2: Disc
10: Bone screw
12: Head part
14: Thread
16: Head tool groove
20: Tool
22: Tool handle 24: Tool rod
26: Tool tip
28: Tool tip guide
100, 101, 103, 105: Cervical plate
102: Plate body
104: Seat part
106: Reinforcing part
108: Round part
110, 111: End stopper
112, 113, 115: Locking element
114: Cutoff part
116: Bending clearance part
118: Locking wing
120: Rotation contact circumference
122: Locking contact circumference
124: Rotation stop circumference
126: Tool guide hole
128: Locking tool groove
130: Rotation body
132: Wing bottom
134: Latching part
136: Concave surface
138: Bone screw hole
140: Body plate beginning part
142: Locking element beginning part
144: Locking element insertion hole
146: Locking element finishing Part
148: Body plate finishing Part
150: Locking jaw

The invention claimed is:

1. A cervical plate comprising:
a plate body formed to extend in a longitudinal direction thereof;
bone screws installed through the plate body;
two or more bone screw holes formed in the plate body to support head parts of the bone screws; and
a locking element configured to maintain the bone screws while being inserted into the bone screw holes, respectively,
wherein the locking element is rotatably mounted in the plate body, and
wherein, when a curvature of the plate body between the locking elements located at opposite ends in the longitudinal direction thereof is R3, and curvatures of the plate body from the locking elements located at opposite ends to the ends thereof are R4 and R5, respectively, the R4 and R5 are smaller than the R3.

2. The cervical plate according to claim 1, wherein the plate body has reinforcing parts formed at outer circumferences thereof.

3. The cervical plate according to claim 1, wherein the plate body has round parts formed at opposite ends in a longitudinal direction thereof.

4. The cervical plate according to claim 3, wherein the round part is formed of two curved surfaces having different radii of curvature.

5. The cervical plate according to claim 4, wherein, when a radius of curvature of a curved surface located at an upper end of the plate body is R1, a radius of curvature of a curved surface located at a lower end of the plate body is R2, a radius of a shank of the bone screw to be inserted into the bone screw hole is L1, and the shortest distance from a central axis of the bone screw to the end of the plate body is L2, the R1, R2, L1 and L2 satisfy Equation 1 below, and R2 is smaller than R1:

$$0.5 \leq \frac{R2 \times L1}{R1 \times L2} \leq 250. \quad \text{[Equation 1]}$$

6. The cervical plate according to claim 1, wherein the plate body has seat parts formed at regions, in which the bone screw holes and the locking elements are disposed, having a thickness thinner than other parts thereof.

7. The cervical plate according to claim 6, wherein the seat part has a depth of less than or equal to a maximum thickness of the locking element.

8. The cervical plate according to claim 1, wherein the plate body has a bending clearance part formed on a lower surface thereof in a direction perpendicular to the longitudinal direction of the plate body.

9. The cervical plate according to claim 8, wherein the bending clearance part has a depth of 0.1 to 0.3 times the thickness of the plate body.

10. The cervical plate according to claim 1, wherein the R4 and R5 are different from each other.

11. The cervical plate according to claim 1, wherein the R4 and R5 are within ranges of 5<R3/R<44, and 5<R3/R5<44.

12. The cervical plate according to claim 1, wherein, when lengths of the plate body occupied by R3, R4 and R5 in the longitudinal direction thereof are L3, L4 and L5, respectively, the L3, L4 and L5 have a ratio of L3:L4:L5=3-5:1:0.8-1.2.

13. The cervical plate according to claim 1, wherein the locking element comprises a rotation body rotatably mounted in the plate body; and a locking wing formed integrally with the rotation body to cover a portion of the bone screw hole.

14. The cervical plate according to claim 13, wherein the rotation body has a tool guide hole formed inside thereof, and a locking tool groove formed on an upper periphery of the tool guide hole concentrically with the tool guide hole.

15. The cervical plate according to claim 13, wherein the locking wing has a rotation contact circumference formed on one side thereof concentrically with the rotation body, and a locking contact circumference formed thereon continued to the rotation contact circumference, such that two adjacent locking elements are independently rotatable in the bone screw hole with abutting each other by the rotation contact circumferences, and further rotation thereof is blocked when the locking contact circumferences are in contact with each other.

16. The cervical plate according to claim 15, wherein the locking wing has a rotation stop circumference formed thereon continued to the locking contact circumference, and a distance between a central axis of the rotation body and the rotation stop circumference is larger than a radius of curvature of the rotation contact circumference.

17. The cervical plate according to claim 13, wherein the locking wing is resiliently deformed with being in contact with a seat part, and is restored to an original shape by an elastic force when covering a portion of the bone screw hole.

18. The cervical plate according to claim 13, wherein the plate body includes the seat parts formed at regions, in which the bone screw holes and the locking elements are disposed, having a thickness thinner than other parts thereof,
wherein a locking element beginning part is formed on a lower surface of the locking wing, and a body plate beginning part is formed on one side of the seat part, and wherein an open state of the locking element is maintained by an engagement between the body plate beginning part and the locking element beginning part unless an external force is applied thereto.

19. The cervical plate according to claim 13, wherein the plate body has an end stopper formed thereon to restrict a rotation of the locking element.

20. The cervical plate according to according to claim 19, wherein a body plate finishing part is formed on the end stopper, a locking element finishing part is formed on a lower surface of the locking wing, and a locked state of the locking element is maintained by the engagement of the body plate finishing part and the locking element finishing part unless an external force is applied thereto.

21. The cervical plate according to claim 13, wherein the plate body has a locking jaw formed thereon in a chevron shape, so as to allow the locking wing of the locking element to climb over the locking jaw while being in contact therewith.

\* \* \* \* \*